(12) United States Patent
Nita

(10) Patent No.: US 9,943,321 B2
(45) Date of Patent: Apr. 17, 2018

(54) METHODS AND DEVICES FOR REMOVAL OF THROMBOEMBOLIC MATERIAL

(71) Applicant: Penumbra Inc., Alameda, CA (US)

(72) Inventor: Henry Nita, Redwood Shores, CA (US)

(73) Assignee: Penumbra, Inc., Alameda, CA (US)

( * ) Notice: Subject to any disclaimer, the term of this patent is extended or adjusted under 35 U.S.C. 154(b) by 370 days.

(21) Appl. No.: 14/682,893

(22) Filed: Apr. 9, 2015

(65) Prior Publication Data
US 2016/0166266 A1 Jun. 16, 2016

Related U.S. Application Data

(63) Continuation-in-part of application No. 14/668,622, filed on Mar. 25, 2015, now abandoned.
(60) Provisional application No. 62/124,406, filed on Dec. 16, 2014.

(51) Int. Cl.
| A61B 17/22 | (2006.01) |
| A61B 17/3207 | (2006.01) |
| A61M 25/10 | (2013.01) |
| A61B 18/14 | (2006.01) |
| A61B 18/00 | (2006.01) |

(52) U.S. Cl.
CPC ...... *A61B 17/22* (2013.01); *A61B 17/320758* (2013.01); *A61B 18/1492* (2013.01); *A61M 25/104* (2013.01); *A61B 2017/22001* (2013.01); *A61B 2017/22067* (2013.01); *A61B 2017/22078* (2013.01); *A61B 2017/22079* (2013.01); *A61B 2017/320775* (2013.01); *A61B 2018/00208* (2013.01); *A61B 2217/005* (2013.01); *A61B 2218/007* (2013.01)

(58) Field of Classification Search
CPC ........... A61B 17/22; A61B 17/320758; A61B 17/3207; A61B 2017/22001; A61B 2017/22079; A61B 17/22012; A61B 17/32056
See application file for complete search history.

(56) References Cited

U.S. PATENT DOCUMENTS

| 6,569,148 | B2* | 5/2003 | Bagaoisan | A61B 17/22 604/101.04 |
| 2010/0049225 | A1* | 2/2010 | To | A61B 17/320758 606/159 |

* cited by examiner

*Primary Examiner* — Victor Nguyen
(74) *Attorney, Agent, or Firm* — Raymond Sun

(57) ABSTRACT

Methods and devices to remove thromboembolic material from the human body using rotational energy and aspiration are disclosed. A thromboembolic removal system includes an extraction device and drive unit. The extraction device is introduced to the treatment area and activated by the drive unit to separate, break apart, loosen or soften thromboembolic material and to facilitate its aspiration outside the patient.

19 Claims, 10 Drawing Sheets

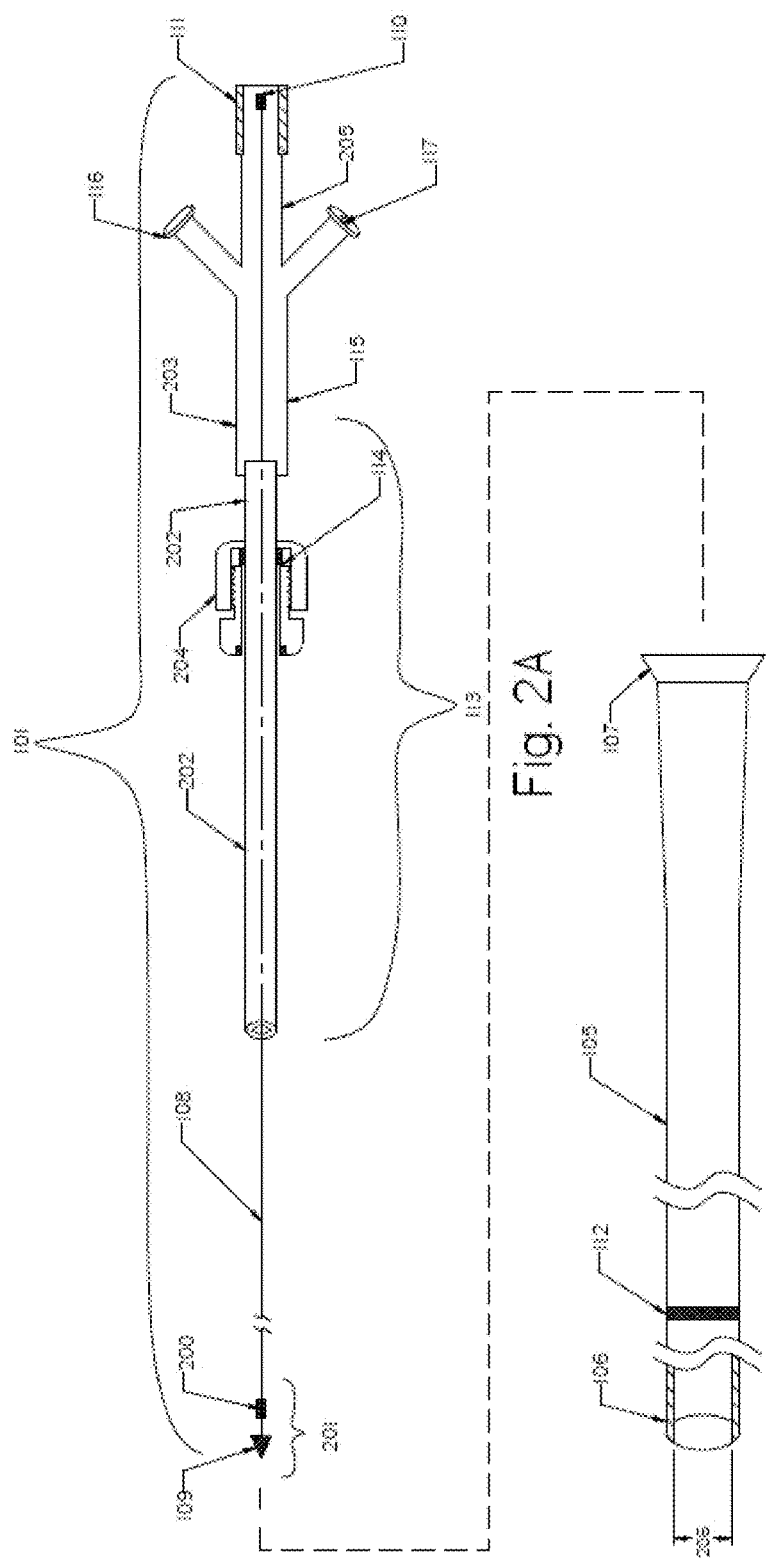

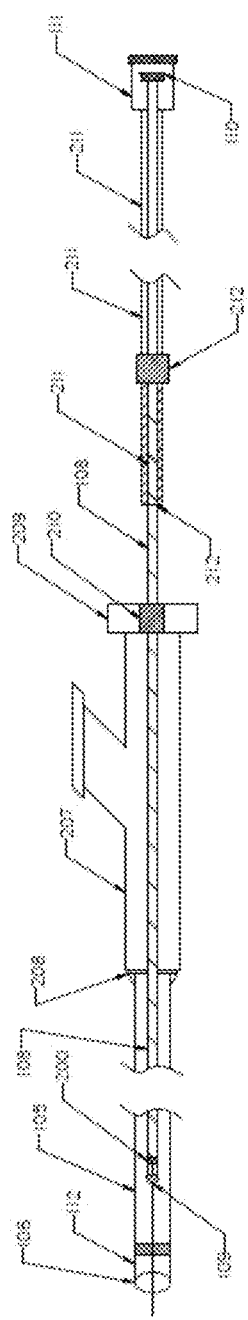
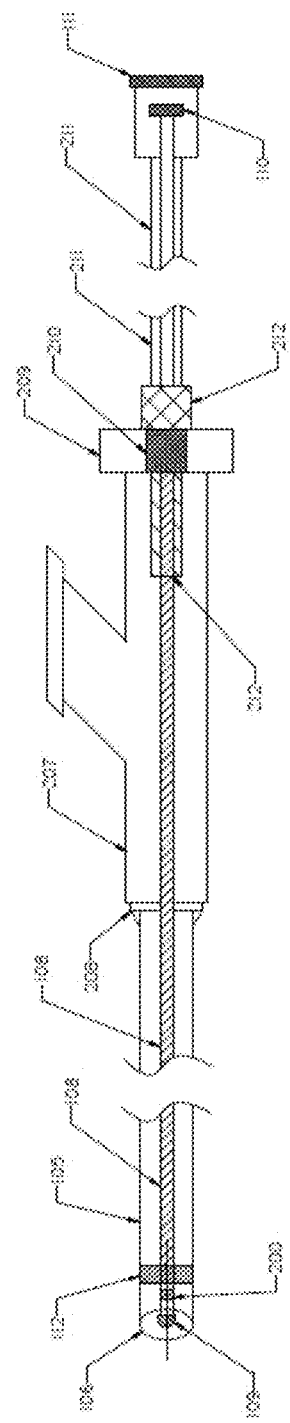
Fig. 2C
Fig. 2D

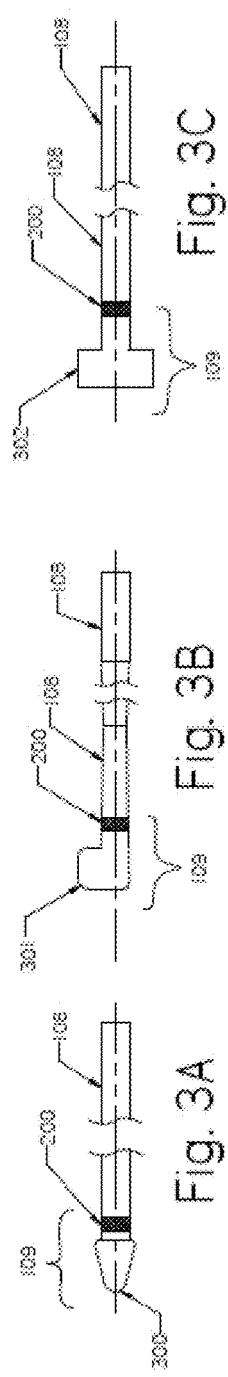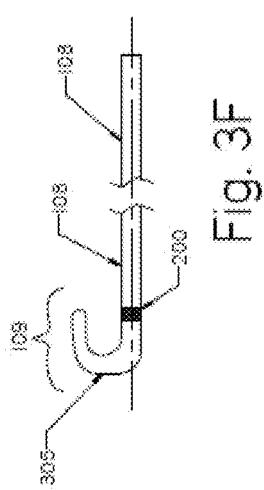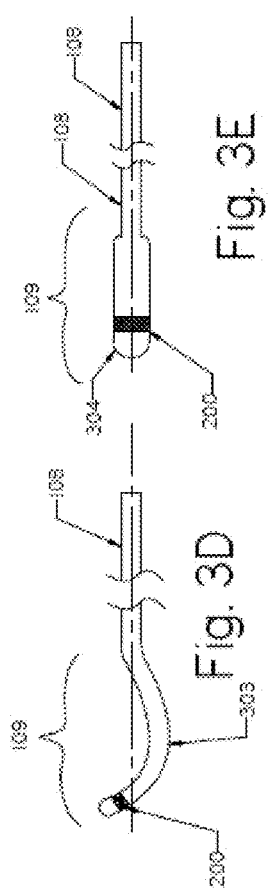

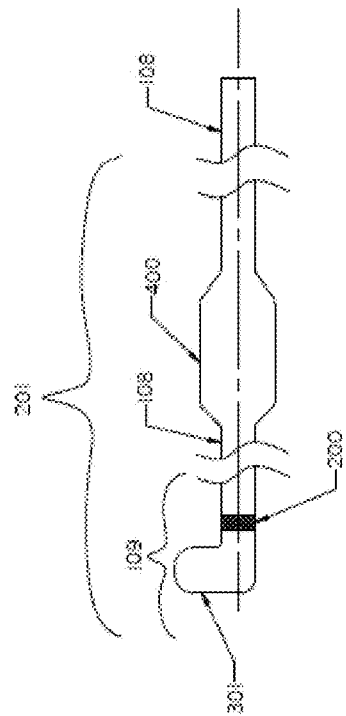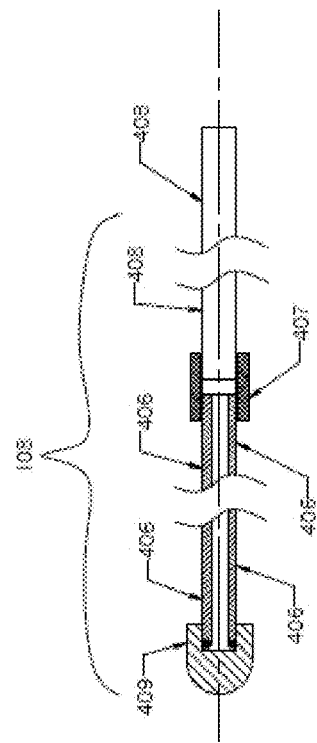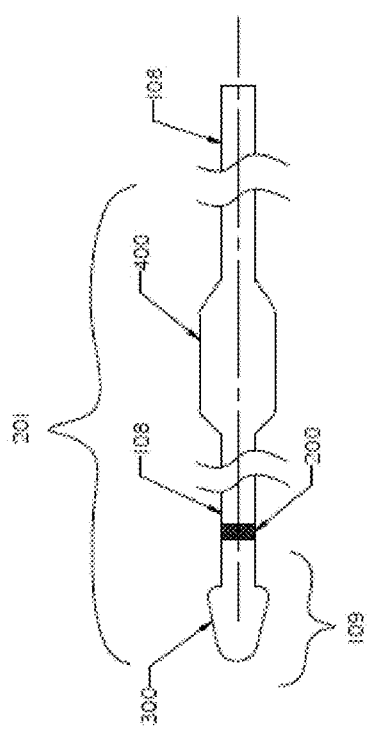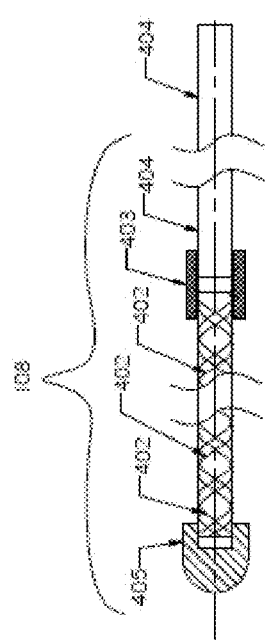
Fig. 4A
Fig. 4C
Fig. 4B
Fig. 4D

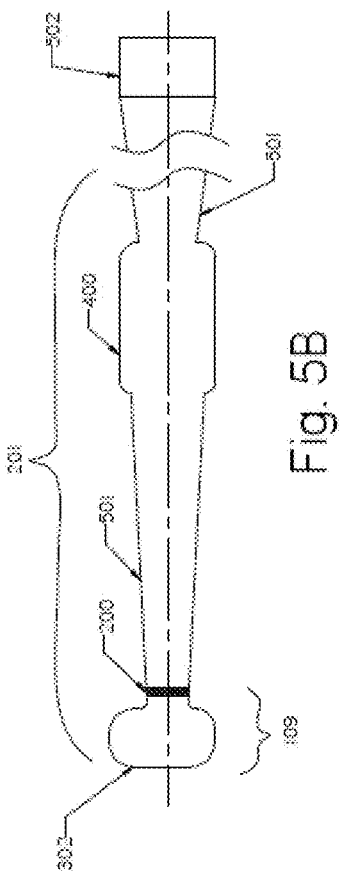
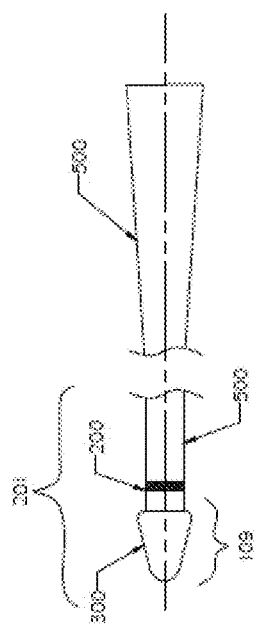
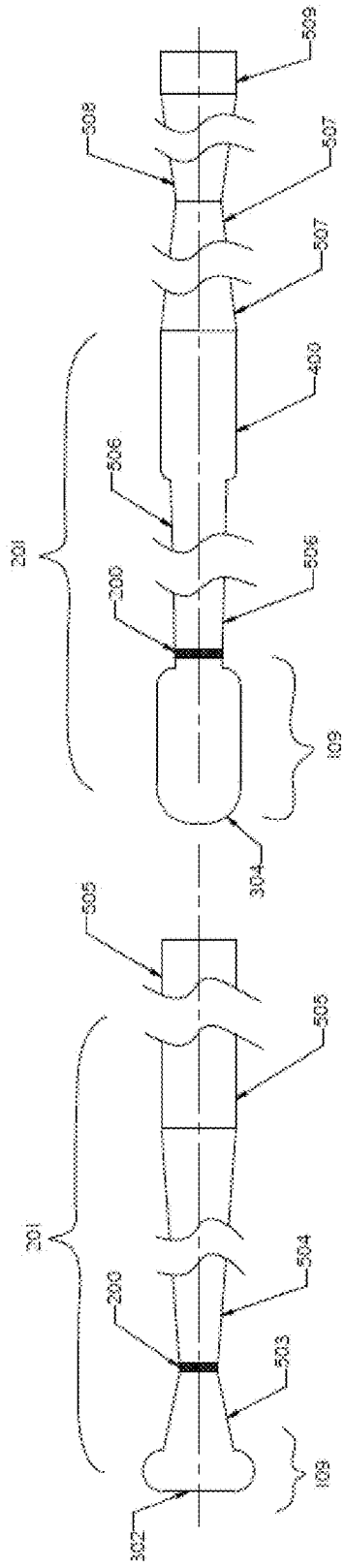
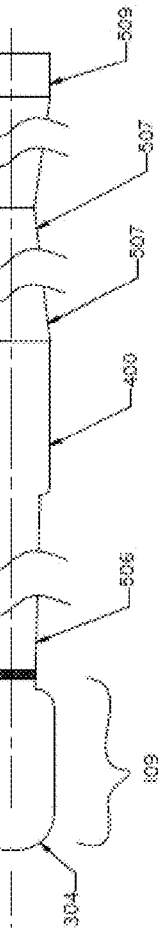

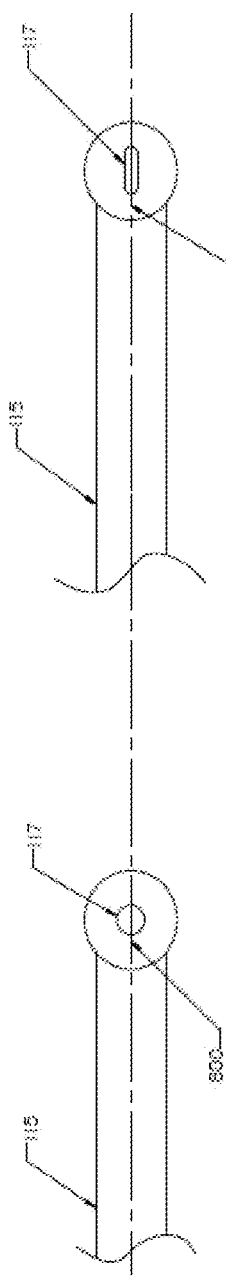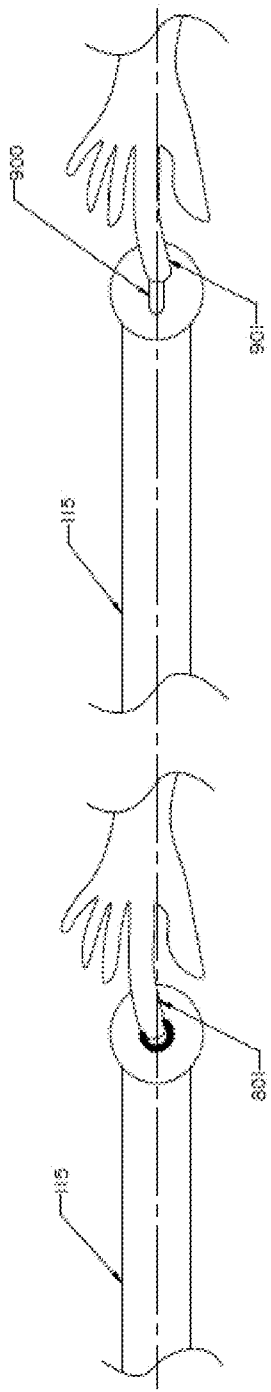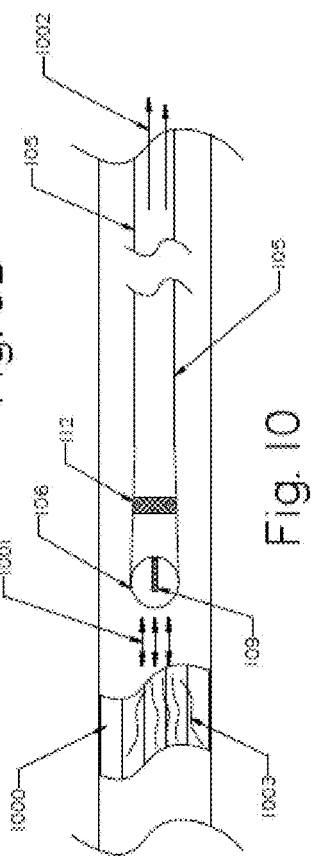

METHODS AND DEVICES FOR REMOVAL OF THROMBOEMBOLIC MATERIAL

RELATED CASES

This application claims priority to U.S. Provisional Application No. 62/124,406, filed on Dec. 16, 2014, and is a continuation-in-part of co-pending application Ser. No. 14/668,622, filed Mar. 25, 2015, whose entire disclosure is incorporated herewith as though fully set forth herein.

BACKGROUND OF THE INVENTION

Field of the Invention

The field of the present application pertains to medical devices. More specifically, the present application is related to devices and methods for removal of thromboembolic obstructing matter from the human endovascular system, including cerebral arteries and other parts of the human body.

Description of the Prior Art

Arterial and venous thromboembolic disease remains a major cause of death and disability despite the discovery of heparin by McLean and Howell in 1916 and its subsequent introduction into clinical practice in 1936. Each year, acute limb ischemia affects 14 persons per 100,000 in the United States population, with procedures relating to the treatment of acute arterial ischemia comprising 10% to 14% of the annual vascular surgical workload. Venous thromboembolism occurs at a fivefold greater frequency with recent estimates of 77.6 cases per 100,000 person-years.

Strokes may be caused by a rupture or bleeding of a cerebral artery ("hemorrhagic stroke"), or a blockage in a cerebral artery due to a thromboembolism ("ischemic stroke"). Intracerebral hemorrhage (ICH) bleeding accounts for approximately 10-12% of all stroke cases in the United States. ICH has long been associated with high rates of morbidity and mortality. Treatment choices for ICH are limited, and the effectiveness of currently available therapies is inadequate. Thrombolytics alone are not recommended, but are currently being investigated for use in conjunction with aspiration and other surgical techniques.

While intracranial hemorrhage is caused by blood clots located outside the blood vessels in the brain, Acute Ischemic Stroke (AIS) is caused by blood clots blocking a blood vessel in the brain arteries. AIS is the third leading cause of death in the United States. Each year, approximately 700,000 people suffer an Acute Ischemic Stroke, and more than 100,000 people die each year in the United States. Nearly three-quarters of all these strokes occur in people over the age of 65. The risk of having a stroke more than doubles each decade after the age of 55. According to the World Health Organization, more than 12 million people suffer Acute Ischemic Stroke worldwide each year. Of these, more than 4 million die and another 4 million are permanently disabled.

Endovascular and outside of endovascular thromboembolic disease remain very widespread causes of death and disability with no ideally effective treatment currently available. Thus, there is a significant need for improved devices, methods and systems for treating thromboembolic disease.

There are many approaches for removing thromboembolic material from the body, either surgical or using catheter devices for endovascular and outside endovascular removal of obstructive matter, such as blood clots, thrombus, atheroma, plaque and the like. These techniques are related to rotating baskets or impellers, cutters, high pressure fluid injections, Archimedes screw, vacuum, rotating wires and other means as described in U.S. Pat. Nos. 4,732,154; 4,737,153; 4,771,774; 4,886,490; 4,883,458; 4,923,462; 4,966,604; 5,041,082; 5,047,040; 5,135,531; 5,180,376; 5,226,909; 5,334,211; 5,376,100; 5,443,443; 5,462,529; 5,485,042; 5,501,694; 5,556,408; 5,569,275; 5,630,806; 5,653,696; 5,695,507; 5,766,191; 5,795,322; 5,843,031; 5,873,882; 5,876,414; 5,911,734; 5,947,940; 5,972,019; 7,037,316; 7,179,269; 7,235,088; 7,666,161; 7,763,010; 7,842,006; 7,842,055; 7,938,820; 7,942,852; 8,062,317; 8,414,543; 8,414,543; 8,535,290 and 8,545,447; and US Applications Nos., 2014/0324080 and 2014/0330286.

Removal of thromboembolic material and blood clots from brain arteries are described in the following U.S. Pat. Nos. 7,063,707; 7,316,692; 7,931,659; 833,796; 8,366,735; 8,460,312; 8,366,735; 8,784,441; 8,801,748, 8,814,892, as well as Simon S. et al., "Exploring the efficacy of cyclic vs. static aspiration in cerebral thrombectomy model: an initial proof of concept study", Journal of Neurointerventional Surgery 2014 November; 6(9): 677-83; among others. Devices and methods disclosed in the prior art include several devices and methods such as: embolectomy devices, clot pullers, retrieving devices or separating devices with aspiration. While most of these devices are capable of removing blood clots from the human arteries, there is still a clinical need for a simple, quick and easy access with devices to the treatment site through tortuous brain arteries, and safe removal of blood clots in a single pass. Often, catheters used to remove clots from brain arteries get clogged after partial removal of clots even under absolute vacuum. In such situations, physicians typically use a "corking" approach to grab the clot with a vacuum and then remove the clogged catheter outside the body to remove the clot. Next they clean the clots from the catheter and navigate the catheter back up to the targeted occlusion to remove the remaining clot. Risks related with device manipulations and multiple accessing of the treatment site, as well as the extended time required for removing blood clots from arteries, may lead to another stroke and have a crucial impact on short and long term clinical outcomes. Thus, there is a need for more efficient and effective devices that facilitate a quick and single pass for the removal of thromboembolic material.

SUMMARY OF THE DISCLOSURE

The devices and methods of the present invention relate to removal of thromboembolic material that include but are not limited to: clots, thrombus, atheroma, fluid, polyps, cysts or other obstructive matter from endovascular system. The endovascular system includes arteries, veins, previously implanted stents, grafts, shunts, fistulas and the like. Removal of thromboembolic materials may also include locations outside of the endovascular system such as: body organs, head, ureters, bile ducts, fallopian tubes, localized tumors, cancerous tissue removal or other particular target site.

In one embodiment the present invention, a thromboembolic system is provided which includes an extraction device and a drive unit. The thromboembolic system can be provided as a single unit with affixed components, or the components of the thromboembolic system may be detachable and attachable before, during or after the thromboembolic material removal procedure.

In another embodiment of the present invention, a method for removing thromboembolic material from a patient using an thromboembolic system having an extraction device and drive unit is provided, the method comprising the steps of identifying the location of a thromboembolic material to be removed, providing an extraction device having an aspiration catheter and a rotational member, positioning the aspiration catheter at the treatment area proximally to the thromboembolic material, inserting the rotational member into the aspiration catheter, the rotational member having an elongate element having a distal tip such that the distal tip of the is adjacent to the distal end of the aspiration catheter, and activating aspiration and rotations of the rotational member to draw thromboembolic material into and through the lumen of the aspiration catheter, and outside the patient. The distal tip of the rotational member rotates along its longitudinal axis and is configured to dissolve thromboembolic material and facilitate its removal outside the patient.

In another embodiment, the rotational member rotates in angular motion distally at 100 to 500,000 RPM, and during rotation, creates centripetal forces at the end of the rotational member.

In another embodiment, the aspiration catheter is either affixed or detachable from the extraction device, and has a continuous inner diameter, and a tapered inner diameter. The aspiration catheter can also have a smaller inner diameter on the distal end with a larger diameter on the proximal end, or a larger diameter on the distal end and a smaller diameter on the proximal end, or combinations thereof.

In some embodiments, the extraction device may be experience reciprocal back and forth movement during the removal of thromboembolic material.

In some other embodiments, the extraction device may be introduced to the treatment area with an attached aspiration catheter, or the aspiration catheter can be disconnected from the extraction device and introduced first to the treatment area using a support device that can include a guidewire, a dilator, a guiding catheter, an introducer, or combinations thereof.

In yet another embodiment, the aspiration catheter may include a single lumen catheter, or a multi lumen catheter, with an additional guidewire lumen provided for rapid exchange, or combinations thereof.

In another embodiment, the aspiration catheter may not be a part of the extraction device, and might include a neurocatheter, a peripheral catheter, a guiding catheter, and an introducer cannula, and have a flexible structure, a partially rigid structure, a fully rigid structure, or any combination thereof along its length.

In some other embodiments, the extraction device may include a rigid distal portion suitable for removal of thromboembolic material from the patient's body and head, and where the rigid portion is made of metal, polymer or a combination of both.

In yet another embodiment, removal of the thromboembolic material may occur from locations within endovascular system, outside of the endovascular system, and combinations of both.

In another embodiment, the aspiration source such is a vacuum pump which is fluidly coupled with the extraction device and the aspiration catheter, and the aspiration can be applied in one of the following modes of operation: continuous mode, ON/OFF mode, modulated mode or combinations thereof.

In yet another embodiment, the extraction device has a side aperture in fluid communication with the aspiration catheter, and vacuum pump to regulate the level of vacuum used for aspiration.

In some embodiments, the aspiration catheter is positioned at the treatment area through an artery, a vein, a surgical aperture or a surgical incision using a femoral approach, a brachial approach, a radial approach, neck incision, a trans-carotid approach, and antegrade to the blood flow or retrograde to the blood flow approaches, as well as an invasive surgical approach including but not limited to a craniotomy and a burr hole.

In some embodiments, the aspiration catheter is deflectable through actuation on the proximal end thereof.

In another embodiment, the rotational member has a shaped distal tip having a larger diameter than the adjacent proximal portion, and is angularly rotated along its longitudinal axis in a continuous mode, ON/OFF mode, modulated mode or combinations thereof.

In another embodiment, the rotational member has one of the following profiles along its length: continuous, tapered in distal direction, tapered in proximal direction, multi tapered and combinations thereof.

In another embodiment, the rotational member is made of metal, metal alloy, polymer or combinations thereof, and comprises one longitudinal element selected from the group consisting of a single solid rod, multiple roads, bundle, tubing, wire strands/cable, coil, braid or combinations thereof.

Rotational members and shafts are mechanical power-transmission devices used to transmit rotary motion through bends and curves. They can be placed inside catheters or sheaths and navigated around complex anatomy which would be otherwise impossible for a solid shaft. Flexible rotational members are made of layers of high-tensile wire wound over each other at opposing pitch angles. When torque is applied to the flexible shaft, the wire layers expand or contract depending on the direction of the rotation. If the torque causes the outer layer to contract, the layer underneath will expand. This creates a dynamic interference between the layers of the cable shaft resulting in high torsional stiffness—several times greater than the sum of the individual layers acting alone.

Flexible rotational members also eliminate alignment problems because they do not require tight tolerances, and in general are 85 to 95% efficient because of low frictional losses. Flexible shafts can run from 0.020 to 1.25 inches in diameter and from 2 inches to 100 feet long. Very-high yield strength is critical in maintaining precise positioning response over many rotations. Yield strength can be as high as 400 lb/inch of torque at speeds reaching more than 18,000 rpm for some applications. Torque will determine the shaft diameter and its construction. A larger diameter typically equates to higher torque capacity. A flexible shaft is made of layers of wires. The number of layers, the number of wires per layer, and the size of the wires within each layer are all variables in flexible-shaft construction. For a given diameter, this construction can be varied to achieve different performance characteristics, including torque, bending flexibility, torsional deflection, axial stretch, bidirectional capability, and other parameters. Directional operation is whether the shaft will be transmitting torque in both directions (bidirectional) or only in one direction (unidirectional). A bidirectional shaft will typically have a construction consisting of many layers of smaller wires. This allows a rotational member to behave similarly in both directions—though it will always be a little stronger in one direction than in the other. If the shaft is required to transmit torque in only one direction, then it will have fewer layers of larger wires, which will make it very strong for the direction of operation and much weaker in the other direction.

The point of helix is the torque load at which the flexible shaft begins to take the shape of a corkscrew or helix. It is always important to operate below this torque level, otherwise stresses within the wires increase and radial forces press the shaft outward against the casing, accelerating friction and wear. All flexible shafts either become longer or shorter when a torque is applied. The degree of change is typically small, but over long shaft lengths, it can become important to account for the axial stretch.

In yet another embodiment, the rotational member has one of the following configurations: circular, oval, square, rectangular, or combination thereof.

In some embodiments, the distal tip of the rotational member has one of the following shapes: arrowed, winged, finned, partial sinusoidal, blade, hook, loop, bend, coils, cable, braid or combinations thereof.

In some embodiments, the portion of the rotational member that is proximal to the distal tip has the one of the following shapes: arrowed, winged, finned, sinusoidal, partial sinusoidal, blade, hook, loop, bend, coil or combinations thereof.

In another embodiment, the rotational member has a distal tip, and the portion immediately proximal to the distal tip has one of the following configurations: continuous configuration, tapered configuration, reversed tapered configuration or combinations thereof.

In another embodiment, the position of the distal end of the aspiration catheter is adjusted relative to the position of the distal tip of the rotational member inside the aspiration catheter so that the relative distance between both ends is within 0 to 10 mm.

In another embodiment, the position of the distal end of the aspiration catheter is adjusted relative to the position of the distal tip of the rotational member outside the aspiration catheter so that the relative distance between both ends is within 0 to 10 mm.

In some embodiments, positioning of the distal tip of the rotational member with respect to the distal end of the aspiration catheter is done using visualization tools, intraoperative imaging, and measurement/localization indicators on one or both devices, such as radiopaque markers.

The present invention may also include monitoring the placement of the aspiration catheter and the rotational member using a monitoring device, such as but not limited to, an image guided navigation system, a computed tomography scan, ultrasound and endoscopes, optiscopes; CT (Computed Tomography), MRI (Magnetic Resonance Imaging), radiographic technologies or Optical Coherence Tomography (OCT), neuro guided-navigational system.

In another embodiment, the gap formed between the rotational member's radial diameter and the inner diameter of the aspiration catheter is between 0 to 5 mm.

In various embodiments, the distal tip of the rotational member can be housed inside the aspiration catheter, outside the aspiration catheter, even with the aspiration catheter, or adjustable between the inside and outside of the aspiration catheter, during the removal of thromboembolic material.

In another embodiment, the distal tip of the rotational member located inside the aspiration catheter is positioned thereto so as to remain in contemporaneous position with the distal end of the aspiration catheter.

In yet another embodiment, the rotational member traverses concomitant bends as the aspiration catheter during introduction to the treatment area, after introduction to the treatment area, during removal of thromboembolic material, and combinations thereof.

In another embodiment, the rotational member moves experiences angular motion distally in an off-centered manner with respect to the aspiration catheter.

In yet another embodiment, the rotational member may rotate clockwise, counter-clock wise or both.

In another embodiment, the rotational member is made of a single rotating member, multimember rotating members or both, in order to aid in breaking up the clot, and preventing the device from clogging during aspiration.

In another embodiment, an extraction device for removing thromboembolic material from a patient comprises an elongated rotational member having a tapered distal portion, an aspiration catheter at least partially surrounding the rotational member and having an aspiration passage, and a fitting assembly positioned on the distal end of the aspiration catheter to adjust the distal end of the aspiration catheter relative to the distal tip of the rotational member. The positioning of the rotational member and the aspiration catheter is configured to change the compliance of the thromboembolic material and to facilitate aspiration thereof outside the patient.

In yet another embodiment of the present invention, a fitting assembly is positioned on the extraction device and attached to the aspiration catheter to adjust the distal end of the aspiration catheter relative to the distal tip of the rotational member. Such positioning of the distal tip of the rotational member and the aspiration catheter provides a wide range of options to safely and more effectively change the compliance of the thromboembolic material to improve the efficacy of the system to remove the thromboembolic material outside the patient.

In yet another embodiment, the positional adjustment of the distal end of the aspiration catheter relative to the distal tip of the rotational member using a fitting assembly can be done any time before, after or during removing the thromboembolic material.

In another embodiment, removing thromboembolic material from a patient is done using centripetal forces, the method comprising positioning an extraction device having an aspiration catheter and rotational member at the location of the thromboembolic material, adjusting the aspiration catheter such that the distal tip of the rotational member is adjacent the distal end of the aspiration catheter and within the distal-most end of the aspiration catheter, activating a vacuum within the aspiration catheter and activating rotations of the rotational member to remove blood clots outside the patient. The distal portion of the rotational member rotates along its longitudinal axis at a speed between 10 to 500,000 RPM, and is configured to break blood clots and to facilitate their aspiration outside the patient.

In another embodiment, Acute Ischemic Stroke is treated using an extraction catheter having an aspiration catheter and a rotational member by a method comprising the steps of identifying the location of thromboembolic material within cerebral vasculature of a patient, introducing an aspiration catheter through an incision to the treatment area, positioning the aspiration catheter proximally to the thromboembolic material, inserting a rotational member into the aspiration catheter, the rotational member comprising an elongate element having a distal tip such that the distal tip of the rotational member is adjacent to the distal end of the aspiration catheter, activating aspiration and rotations of the rotational member to draw thromboembolic material into and through the lumen of the aspiration catheter, and outside the patient. During this method, the distal tip of the rotational member applies centripetal forces to facilitate the removal of thromboembolic material outside the patient.

In another embodiment, irrigation is provided at least partially around the rotational member and within the aspiration lumen to further facilitate the removal of thromboembolic material.

In yet another embodiment, additional aspiration is provided proximally to the treatment area via an additional catheter or guiding catheter to further prevent small emboli dislodgment during the removal of blood clots and other tissue.

In another embodiment, the aspiration catheter and the rotational member are configured to deliver radiofrequency energy for blood vessel or tissue cauterization when necessary. Occasionally, during the removal of thromboembolic material from outside of the endovascular space such as ICH, additional bleeding may occur. Such bleeding is often caused by bleeding of non-effected vessels from the original bleed or from re-bleeding from the affected vessels. This new bleeding may cause another hemorrhagic stroke. To minimize additional blood-loss and prevent exsanguination, a cauterizing approach may be used, including but not limited to electro cautery, ultrasound cautery and chemical cautery. Electro-cauterization is preferable to other forms of cauterization because it will not leach into neighboring tissue and cauterize outside of the intended boundaries.

In another embodiment, an occlusion balloon is deployed and expanded within the blood vessel to occlude the vessel around the treatment area to secure a more effective aspiration of the thromboembolic material outside the patient.

In yet another embodiment of the present invention, the thromboembolic system includes an extraction device and a drive unit including an aspiration pump and an electrical motor. The whole system can be disposable, single-use or part of the system may be reusable, such as the drive unit.

In some embodiments, the method of removing thromboembolic material may involve delivering pharmacologic agent to the treatment location. Such agents may include, but are not limited to: tissue plasminogen activator, blood clot reducing agents, antiplatelet agents, and other GIIb/IIIa inhibitors.

Some thrombectomy techniques employ aspiration alone to mechanically entrap and extract clots. Other techniques use aspiration in conjunction with clot retrievers or macerators to dislodge clots from the treatment location and aspirate outside the body. Aspiration techniques operate either using vacuum pumps or conventional syringes. While syringes are efficient in the aspiration of small amounts of fresh clots, suction pumps are often used to remove larger and well-organized clots. Suction pumps operate in the following modes including: static suction (a continuous pressure suction), modulated suction (vacuum increase/decrease suction), pulse suction (ON/OFF suction) or a combination thereof. Use of a static suction is well known in the art and mostly relies on a high vacuum pressure; a higher vacuum pressure level produces higher efficacy. However, in some applications where clots are larger than the catheter or cannula diameter, and the clot is well organized, the catheter or cannula is often clogged and requires device removal and cleaning. Examples of such applications include but are not limited to Acute Ischemic Stroke or Intracranial Hemorrhage. Using aspiration pulsation or modulation may improve device efficacy either using aspiration alone or in conjunction with other mechanical enhancements. Exposing clots to aspiration pressure pulsation or modulation will induce feebleness, fatigues, fracture and micro-cracks within the clot structure, thereby changing the compliance of the clots and enabling or facilitating removal of the clots outside the patient.

Many experimental studies in the last decade have confirmed that moderate hypothermia show protection against ischemic and non-ischemic brain hypoxia, traumatic brain injury, anoxic injury following resuscitation after cardiac arrest and other neurological insults including Acute Ischemic Stroke (AIS). Many adverse events that occur in the injured brain at a cellular and molecular level are highly temperature-sensitive and are thus a good target for induced hypothermia. The basic mechanisms through which hypothermia protects the brain are clearly multifactorial and include at least the following: reduction in brain metabolic rate, effects on cerebral blood flow, reduction of the critical threshold for oxygen delivery, blockade of excitotoxic mechanisms, calcium antagonism, preservation of protein synthesis, reduction of brain thermopooling, a decrease in edema formation, modulation of the inflammatory response, neuroprotection of the white matter and modulation of apoptotic cell death. Induced hypothermia may modulate neurotoxicity and, consequently, may play a unique role as an adjunctive therapy for treating brain injury after AIS and improving its devastating effects. The lowering of body temperature between 32-34° C. may be accomplished by many means including the use of cooling blankets, cooling helmets, endovascular cooling catheters, ice packs and ice water lavage. Use of hypothermia in conjunction with embodiments of the present invention may have a broad therapeutic use in the future.

As used herein: "rotational member" and "rotating member" of the device for removal of obstructive material from the patient refer to the same component. In addition, as used herein: "thromboembolic material removal system" and "thromboembolic system" refer to same component. "Aspiration", "vacuum" and "suction" also refer to the same action. "Aspiration pump", "vacuum pump" and "suction pump" refer to the same component. "Continuous aspiration" and "static aspiration" also refer to the same action.

BRIEF DESCRIPTION OF THE DRAWINGS

Certain preferred embodiments and modifications thereof will become apparent to those skilled in the art from the detailed description below having reference to the figures that follow.

FIGS. 2A-2B is cross-sectional view of the extraction device as shown in FIG. 1 with the aspiration catheter detached from the extraction device.

FIG. 2C is a cross-sectional view of a conventional Y-connector located on the aspiration catheter.

FIG. 2D is a cross-sectional view of a conventional Y-connector located on the aspiration catheter with the rotational member fully secured inside the aspiration catheter.

FIGS. 3A-3H show alternative tip configurations for the rotational member.

FIGS. 4A-4D show alternative configurations the rotational member.

FIGS. 5A-5D show alternative configurations of the rotational member.

FIGS. 8A-8B illustrate an ON/OFF aperture within the extraction device for vacuum pulsation.

FIGS. 9A-9B illustrate a longitudinal incision aperture in the extraction device for vacuum modulation.

FIG. 10 illustrates the distal end of the extraction catheter at the location of the clot when aspiration pulsation or modulation is applied.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

Figure 1:
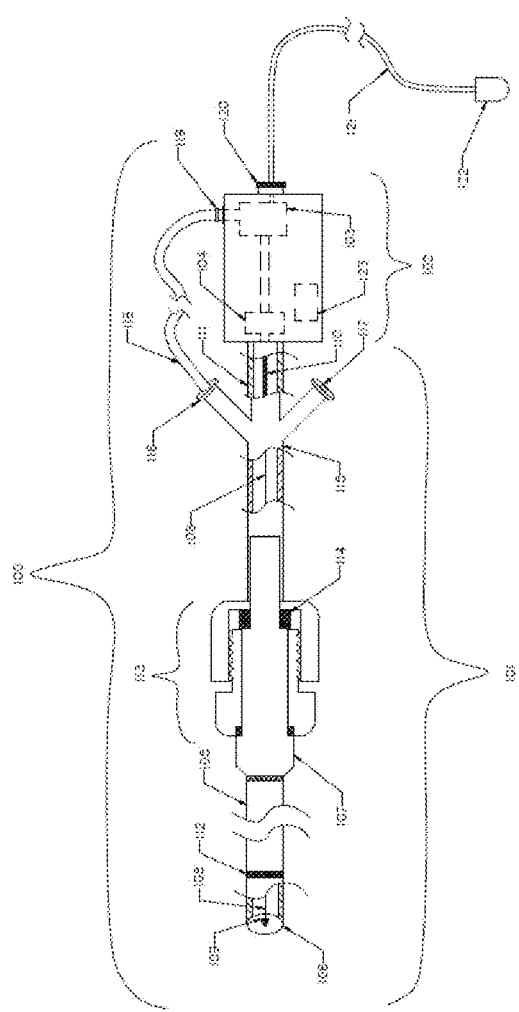
FIG. 1 is a perspective view of a thrombotic material removal system according to the present invention.

As used herein, "rotational member", "cable", "cable shaft", "rotating member" all refer to the mechanical power-transmission devices used to transmit rotary motion through a straight treatment access, as well as through bends and curves FIG. 1 illustrates an exemplary embodiment of a thromboembolic removal system 100. The thromboembolic removal system 100 includes two major components: the extraction device 101 and the drive unit 102. The drive unit 102 includes at least one vacuum pump 103 to aspirate thromboembolic material, and an electrical motor 104. The main components of the extraction device 101 include an aspiration catheter 105 having a distal end 106 and a proximal end 107, a rotational member 108 which is longitudinally extended through the extraction device 101. The rotational member 108 has a distal end/tip 109 and a proximal end 110 that is located inside a connector 111. The proximal end 110 of the rotational member 108 is attached via the connector 111 to the motor 104 located inside the drive unit 102. There is a radiopaque marker 112 located on the distal end 106 of the aspiration catheter 105.

The extraction device 101 also includes a fitting assembly 113 having a seal 114, and a three-way Y-connector 115 having an aspiration outlet 116 and a fluid communication aperture 117 to regulate aspiration applied to the aspiration catheter 105. The aperture 117 is opened and closed based on procedural vacuum requirement using the operator's finger. The aspiration outlet 116 located on the extraction device 101 transports thromboembolic material through a tube 118 (which is coupled to the outlet 116) into an inlet 119 of the drive unit 102. Thromboembolic material is further transported through the drive unit 102, the outlet 120 in the drive unit 102, and a tube 121 into a disposal bag 122.

The connector 111 located at the proximal end of the extraction device 101 supports connection of the proximal end 110 of rotational member 108 to the motor 104 located inside the drive unit 102. There are many optional connection methods that can be used to connect the distal end 110 of the rotational member 108, and for that matter, the extraction device 101, to the motor 104 located inside the drive unit 102, including but not limited to conventional screws, snaps, and female/male interfaces. Such connection of the extraction device 101 to the drive unit 102 is convenient for packaging and handling since both parts are provided separately and attached by the operator before the use. Also, the extraction device 101 and the drive unit 102 can be permanently fixed or connected together and provided as one disposable unit. The drive unit 102 may either contain (or be attachable to) a power source. For example, in some embodiments, the drive unit 102 may be attached to an electrical cable (not shown) that can be plugged into a wall outlet. In other embodiments, the drive unit 102 may include one or more disposable or rechargeable batteries 123 to power the pump 103 and the motor 104.

While the electrical motor 104 is shown and described in FIG. 1, other devices that translate, oscillate, reciprocate, vibrate and/or the like may be substituted for the motion of the rotational member 108. Thus, the operation of the thromboembolic material removal system 100 is not limited to rotational movement alone.

In connection with the system of FIG. 1, various components described herein may be provided as part of the thromboembolic system 100 for removing thromboembolic material, including but not limited to an introducer, a guide catheter, a dilator, an occlusion balloon catheter, a trocar, as well as other tools appropriate for the procedure.

When the aspiration catheter 105 is attached to the extraction device 101 as shown in FIG. 1, an entire extraction device is fluidly coupled between the distal end 106 of the aspiration catheter 105 and the aspiration outlet 116. The aperture 117 serves to regulate the level of vacuum that is applied to the distal end 106 of the aspiration catheter 105.

As will be described in greater detail below, the thromboembolic removal system 100 advantageously provides the ability to remove thromboembolic material from an endovascular and outside of the endovascular system within a patient while overcoming the drawbacks and limitations of the prior art.

FIGS. 2A-2B is a cross-sectional view of the extraction device 101 as shown in FIG. 1 with the aspiration catheter 105 detached from the extraction device 101. As shown in FIG. 2A, a radiopaque marker 200 is located on the distal portion 201 of the rotational member 108. Such a radiopaque marker is not necessary if the distal tip 109 of the rotational member 108 is made of radiopaque material. The marker 112 at the distal end of the aspiration catheter 105 and the marker 200 located at the distal end of the rotational member 108 function to position the extraction device 101 at the treatment site, and to align the distal end 106 of the aspiration catheter 105 with respect to the distal tip 109 of the rotational member 108.

The proximal end 107 of the aspiration catheter 105 in FIG. 2B may be connected and disconnected from the fitting assembly 113 of the extraction device 101. The aspiration catheter 105 may be permanently attached to the extraction device 101 when treatment sites are located in locations that are easier to access. If treatment locations are in areas that are tortuous and difficult to access, for example in patient cerebrovascular circulation, the aspiration catheter 105 can be disconnected from the extraction device 101 and introduced to the treatment area first. Also, the aspiration catheter 105 may be provided separately from the extraction device 101. In such a case, the aspiration catheter 105 may be a catheter such as a neurocatheter, a peripheral catheter, or a guiding catheter, as shown in the FIGS., or the aspiration catheter 105 may be embodied in the form of an introducer or cannula, or other similar device.

The aspiration catheter 105 having the inner distal lumen 206 may have a fixed diameter, distally tapered diameter or combination of all (not shown The aspiration catheter 105 may have a flexible structure along its length, such as a rigid structure, a partially rigid structure, or combination of both, at along its entire length, or along different sections thereof. Also, when needed to navigate difficult anatomies, the distal end 106 of the aspiration catheter 105 can also be provided to be a deflectable distal end 106 by using an actuation feature positioned on the proximal end 107 of the aspiration catheter 105 (not shown) and attached to the fitting assembly 113 if necessary. Such actuation features are known in the art.

The fitting assembly 113 consists of a tube 202 made of metal or polymer, and a Touhy-Borst valve/adapter 204. The rigid tube 202 is permanently attached to the distal portion 203 of the Y-connector 115 and it partially surrounds the rotational member 108. The Touhy-Borst valve 114 is positioned on the tube 202. Measurement marks may be incorporated on the tube 202 (not shown) to allow longitudinal and precise adjustment/movement of the Touhy-Borst valve 204 with the attached aspiration catheter 105 along the tube 202.

Touhy-Borst valves are well known in the medical device field and often are used to seal other devices, mostly guidewires and catheters, that are introduced inside the body to prevent back flow of blood. Examples of such devices include but are not limited to Touhy-Borst valve model 80330 from Qosina, Edgewood, N.Y. The Touhy-Borst valve 204 is positioned around the tube 202 such way that it can be repositioned along the tube 202 as desired. The proximal end 106 of the aspiration catheter 105 is attached to the Touhy-Borst valve 204 so it can move back and forth along the tube 202 as well. Repositioning the Touhy-Borst valve 204 with an attached aspiration catheter 105 along the tube 202 will move the flexible catheter 105 longitudinally along the rotational member 108. This movement allows the distal end 106 of the aspiration catheter 105 to be accurately positioned relative to the distal tip 109 of the rotational member 108 as needed. Once the distal end 106 of the aspiration catheter 105 is at the desired position with respect to the distal tip 109 of the rotational member 108, the Touhy-Borst valve 114 is tightened around the tube 202, which squeezes the seal 114 inside the Touhy-Borst valve 204 and around the tube 202 at a fixed position/location along the tube 202.

In FIG. 2C, a conventional Y-connector 207 having a distal end 208 is attached to the aspiration catheter 105. The proximal portion 209 of the Y-connector 207 has a valve 210. The distal portion of the rotational member 108 is introduced (partially or fully) through the proximal valve 210 of the Y-connector 207 and inside the aspiration catheter 105. On the proximal portion of the rotational member 108 there is an additional tube 211 having a distal end 212 that is still outside the valve 210 of the Y-connector 207. The tube 211 may be made of polymer or metal. There is a stopper 212 affixed to the tube 211. The stopper 212 can be made of polymer or metal and serves to position the tube 211 at a specific location inside the Y-connector 207. When the stopper 212 reaches the proximal end 209 of the Y-connector 207, it cannot be moved inside the valve 210. A very proximal portion 110 of the rotational member 108 and the connector 111 together function to connect the rotational member 108 to the power drive/motor (not shown).

In FIG. 2D, the rotational member 108 is fully positioned inside the aspiration catheter 105. The stopper 212 is at the proximal end 209 of the Y-connector 207, and the distal end of the rotational member 108 is positioned at the distal end 106 of the aspiration catheter 105. The tube 211 is positioned inside the Y-connector 207. The stopper 212 is aligned such way that it prevents extensive exposure of the distal tip 209 of the rotational member 108 outside the distal end 106 of the aspiration catheter 106. To further prevent the often undesirable exposure of the distal tip 109 of the rotational member 208 outside the distal end 106 of the aspiration catheter 105, an angiographic adjustment can be made to assure that the marker 200 located on the distal tip 109 of the rotational member 108 is aligned with the marker 112 located on the distal end 106 of the aspiration catheter 105.

Positioning of the distal end 106 of the aspiration catheter 105 using the alignment of the Touhy-Borst valve 204 along the tube 202 can be performed anytime during or before the thromboembolic material removal procedure. The tube 202 should be long enough so that a desirable distance can be maintained between the distal tip 109 of the rotational member 108 and the distal end 106 of the aspiration catheter 105 when the distal tip 109 of the rotational member 108 is inside the aspiration catheter 105 or outside the aspiration catheter 105. The Touhy-Borst valve 204 is always located on the tube 202 to guarantee a seal when it is tightened after positioning, and during aspiration and thromboembolic material removal. The tube 202 is fluidly connected with the aspiration catheter 105 and the aspiration outlet 116 of the extraction device 101.

Other alternative embodiments to control the position of the distal tip 109 of the rotational member 108 with respect to the distal end 106 of the aspiration catheter 105 may include, but are not limited to: placing applicable spacers or inserts on the rotational member 108 inside the extraction catheter 101 between the proximal end 107 of the aspiration catheter 105 and the Y-connector 207 (not shown); providing the connector 111 with an adjustable length, so the overall length of the rotational member 108 may be adjusted (longer or shorter) with respect to the distal end 106 of the aspiration catheter 105 as desired any time before or during thromboembolic material removal; and any other suitable methods and solutions.

If the drive unit 102 is a reusable unit and is located outside the sterilized field, an extension tube may be attached to the proximal end 205 of the Y-connector 115 and a longer rotational member 108 can be extended through the extension tube. Such extended rotational member 108 will be attached to the motor 104 the same manner as described above.

The rotational member 108 that is connected to the motor 104 is configured to move in angular motion longitudinally. The rotational mode may include but it is not limited to: continuous rotations, ON/OFF rotations, modulated rotations, or combinations thereof. A rotational speed may be anywhere within 100-200,000 RPM. The rotational member 108 may be made at least partially from metal, metal alloys, polymer or combinations of the above (e.g., composites), and may have a cross-sectional contour that is shaped as circular, oval, square, rectangular, or combinations thereof. The rotational member 108 may be a single solid rod or wire, a multiple solid rod or wires, tubing, cable, strands, coil, braid or combinations thereof along its length.

The rotational member 108 of the extraction device 101 may also be attached in an off-centered manner with respect to the motor 104 to provide an off-center angular motion of the rotational member 108.

When the distal tip 109 of the rotational member 108 rotates, it follows a circular path and is accelerating because the velocity is constantly changing directions. Accelerations are caused by forces acting on the rotating tip 109 and are called the centripedal forces or "center seeking" forces which means that the force is always directed towards the center of the circle. The centripetal forces are based on three factors: (i) the velocity of the object as it follows the circular path; (ii) the object's distance from the center of the rotating path; and (iii) the mass of the object. When thromboembolic material is vacuumed into the distal end 106 of the aspiration catheter 105 and the distal tip 109 of the rotational member 108 rotates in a circular motion, the rotating tip 109 will enable thromboembolic material separation, partition and will facilitate its aspiration proximally.

If necessary, electro-cauterization may be performed before, during or after thromboembolic material removal using the extraction device 101. Radiofrequency energy maybe delivered to the distal portion 201 of the rotational member 108 including the distal end/tip 109 of the rotational member 108 and to the treatment area. If the aspiration catheter 105 of the extraction device 101 has a metallic portion included distally (not shown), it also can serve to deliver radiofrequency energy to the treatment area.

FIGS. 3A-3F illustrate several alternative embodiments of the distal tip 109 of the rotational member 108. FIG. 3A shows an arrow-shaped distal tip 300. FIG. 3B shows a fin-like distal tip 301 with an enlarged extending from one side. FIG. 3C shows a winged distal tip 302 that resembles a hammer-head. FIG. 3D shows a curved distal tip 303. FIG. 3E shows a blade-like distal tip 304 where the tip 109 is enlarged along a short length. FIG. 3F shows a looped distal tip 305 that resembles a hook. Other shapes are also possible for the distal tip 109, such as a partial (quarter or half) sinusoidal or full sinusoidal shape, baskets, and a variety of bends. All of these embodiments may be formed as part of (i.e., in one piece with) the distal tip 109 of the rotational member 108 as shown in FIGS. 3A-3F. Alternatively, as shown in FIGS. 3G and 3H, the distal tip 109 can be provided as additional components that are attached to the distal tip 109 using known techniques such as bonding, welding, soldering, crimping, fusing or any other suitable and similar techniques. Such components for the distal tip 109 may be made of metal, polymer, rubber, ceramic, or combinations thereof. Any configuration of the distal tip 109 of the rotational member 108 that can effectively disintegrate thromboembolic material within the entry into the aspiration catheter 105, or effectively facilitates removal of thromboembolic material within the aspiration catheter 105 can be used for this application. As shown in FIGS. 3A-3F, the distal tip 109 may have shapes that are larger than the adjacent proximal portion of the rotational member 108. As shown in FIGS. 3A-3F, the overall dimension of the primary configuration at the distal tip 300, 301, 302, 303, 304 and 305 is larger than dimension of most adjacent proximal portion of the rotational member 108.

FIG. 3G shows a distal tip 306 that is attached to the distal end of the rotational member 108 and is considered the distal tip 109 of the rotational member 108. Such a tip 306 can be made of any of the materials described above, and attached to the rotational member 108 using any suitable technique known in the art, including but not limited to bonding, welding, crimping, and soldering. The distal tip 306 shown in FIG. 3G has a straight configuration with a rounded tip.

FIG. 3H shows another embodiment of a distal tip 307 that can be attached to the rotational member 108. The distal tip 307 is configured with a bend that is bent at an angle of a.

FIGS. 4A-4B show alternative configurations for the distal portion 201 of the rotational member 108, and are referred to herein as the primary and secondary configurations. The primary configurations are located on the distal tip 109 of the rotational member 108 while the secondary configurations are located proximally to the primary configurations along the rotational member 108. These embodiments are illustrative and include but are not limited to any of the single or multiple shape configurations described above, either formed or attached at the distal tip 109 of the transmission member 108, formed or attached proximally to the distal tip 109 of the rotational member 108, or any combination thereof.

FIG. 4A shows an arrow-shaped distal tip 300 for the distal tip 109, and additional blade-shaped expanded section 400 located proximally to the arrow-shaped distal tip 300. The distance between the arrow-shaped distal tip 300 and the section 400 can range from 0 mm to 200 mm, and is preferably within 5 mm-50 mm.

FIG. 4B shows another embodiment that includes a fin-like distal tip 301 and an additional blade-shaped expanded section 400 located proximally to the fin-like distal tip 301. As shown in FIGS. 4A-4B, the dimensions of the primary configuration at the tip 300 and 301 and secondary configurations 400 and 401 are larger than dimension of the most adjacent proximal portion of the rotational member 108. All configurations of the distal portion of the rotational member 108 shown in FIGS. 3A-3F and FIGS. 4A-4B have a continuous dimensional size. Such dimensional size may continue along the entire length of the rotational member 108, or have a tapered or stepped transition into a larger or smaller size proximally.

For treatment areas with a difficult access, such as the cerebral or distal peripheral vasculature, a more compliant structure can be used for the rotational member 108, such as a cable or other multi-wired constructions. A cable is a flexible element whose sub-elements are stranded together such that all of the strands share the load: either rotational torque, bending stress, longitudinal tensile or both. Cables can comprise two or more wires running side by side, bonded, twisted, or braided together that form a single assembly. One end of the cable can be connected to a rotational device and the other left free for rotation.

A great advantage of using cable for that rotational member 108 is that cable may undergo complex bends and are literally compliant, which allows them to be forgiving of misalignment. Also, when a cable passes around complex anatomy, bending stress in any single strand is far lower than in a rod or wire of the same diameter if exposed to the same bends. While cable for the transmission of rotational motions is used primary in low speed applications, use of polymer coatings or jackets would further reduce rotational friction and may be applicable for a higher speed. The most important feature of the cable-driven rotational motion is that a cable can bend in three dimensions. Such characteristics make cables very unique motion transmitters for endovascular and any other medical applications. Often, polymer strand(s) are used within cable structures such as Kevlar™ as an elastic backup.

FIGS. 4C-4D illustrate alternative configurations of the rotational member 108 including cables and multi wires.

FIG. 4C shows a cable 402 attached to a rod, wire or tube 404 via attachment member 403. Such cables are usually made of metal or metals alloys, including but not limited to SST, Nitinol, Titanium, Silver, Copper, Inconel™ and others, with the addition of Kevlar™, Vectran™ and coated with PTFE, FEP, Nylon and other polymers. Several cable configurations maybe used for the current invention, including but not limited to 1×3 strand (one bundle with e wires), 1×7 strand (one bundle with seven wires), 3×7 strand (three bundle with 7 wire), 1×19 strand (one bundle with 19 wire), and many other combinations known in the art for industrial applications. The cable 402 is connected to the rod, wire or tube 404 via the connecting element 403 by bonding crimping, welding, soldering and other known methods. The cable 402 can also be directly attached to the rod, wire or tube 404 without an attaching element 403 using similar attachment methods. Also, the cable 402 may be a single element serving as an entire rotational member 108. There is a cap 405 attached to the distal end of the cable 402. The cap 405 can be formed using any of the configurations shown in FIGS. 3A-3H and FIGS. 4A-4B, and 5A-5D (described below).

FIG. 4D shows a straight wire bundle 406 having two wires that are connected to a rod, wire or tube 408 via a connector 407. Such a bundle 406 may include two or more straight wires, either connected to each other, partially connected to each other, or totally independent (i.e., not connected to each other). The wire bundle 406 can be covered with a polymer sheath to provide a low-friction cover when needed. A cap 409 may be attached to the distal end of the wire bundle 406. The advantage of using a straight wire bundle on the distal end of the rotational member 108 is that a bending stress in any single wire is far lower than in a wire of the same diameter if exposed to the same bends. While the embodiment of FIG. 4D does not belong to the categories of cables/strands, it can also be a very suitable and useful vehicle to deliver rotational motion around complex curves. Caps 405 and 409 may not always be required, and in such a case, a natural structure of the cable (FIG. 4C) and two wires (FIG. 2D) could serve as the distal tip of the rotational member.

FIGS. 5A-5D illustrate alternative embodiments of the distal portion 201 of the rotational member 108. FIG. 5A shows an arrow-shaped tip 300 positioned on the distal tip 109 of the rotational member 108 and having a tapered segment 500 proximally adjacent to the tip 300. Such a tapered portion 500 of the rotational member 108 can continue along the rotational member 108, or have a tapered or stepped transition into a larger or smaller size proximally.

FIG. 5B shows a winged distal tip 302 positioned on the distal tip 109 of the rotational member 108 and having a tapered segment 501 proximally adjacent to the tip 302. There is a secondary blade-shaped expanded section 400 located on the tapered portion 501 of the rotational member 108. The tapered portion 501 of the rotational member 108 may transition into a continuous portion 502. The tapered portion 501 can also continue along the rotational member 108 or have a tapered or stepped transition into a larger or smaller size proximally.

FIG. 5C shows a winged distal tip 302 located on the distal tip 109 of the rotational member 108. The distal-most portion 503 of the rotational member 108 has a reverse taper. The immediate proximal portion 504 of the rotational member 108 has a conventional taper (smaller to larger) configuration. The tapered immediate proximal portion 504 of the rotational member 108 may transition into a continuous portion 505.

FIG. 5D shows a blade-like distal tip 304 located on the distal tip 109 of the rotational member 108. The distal-most portion 506 of the rotational member 108 has a tapered configuration. The secondary shape provides a blade-shaped expanded section 400 that is located on the tapered portion 506. The proximal segment 507 to the secondary blade 400 has a reverse taper that transitions into a conventional taper 508. The tapered portion 508 of the rotational member 108 may transition into a continuous portion 509, or continue as a taper along the rotational member 108, or have a tapered or stepped transition into a larger or smaller size proximally.

The combinations and numbers of the primary and secondary configurations that can be implemented on the distal portion 201 of the rotational member 108 may vary. In one embodiment, there might be no primary shape at all, and one or more secondary shapes; in another embodiment, there might be one primary shape and no secondary shape; in yet another embodiment, there might one primary shape and one or more secondary shapes; and so on.

Figure 6A:
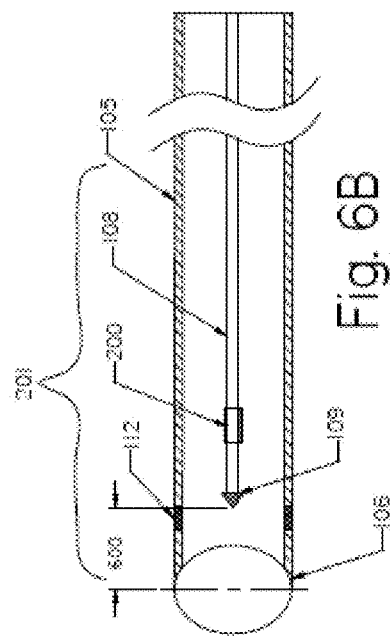
FIG. 6A shows the distal end of the rotational member positioned even with the distal end of the aspiration catheter.

FIG. 6A shows the distal tip 109 of the rotational member 109 in a flush position with the distal end 106 of the aspiration catheter 105.

Figure 6B:
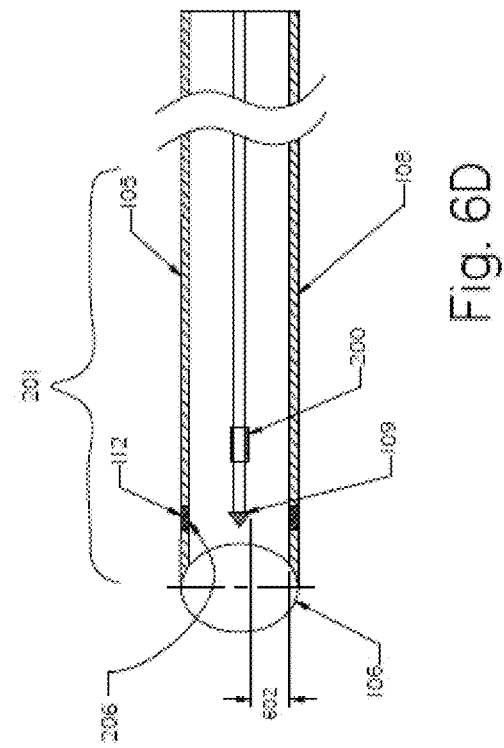
FIG. 6B shows the distal end of the rotational member positioned inside the aspiration catheter.

FIG. 6B shows the distal end 106 of the aspiration catheter 105 and the distal portion 201 of the rotational member 108. The distance 600 between the distal tip 109 of the rotational member 108 and the distal end 106 of the aspiration catheter 105 when the distal tip 109 is inside the aspiration catheter 105 can range between 0.0 mm and 50 mm, most preferably between 0.0 mm and 5 mm as measured using the fitting assembly 113 or any suitable visualization, intraoperative imaging, or other means.

Figure 6C:
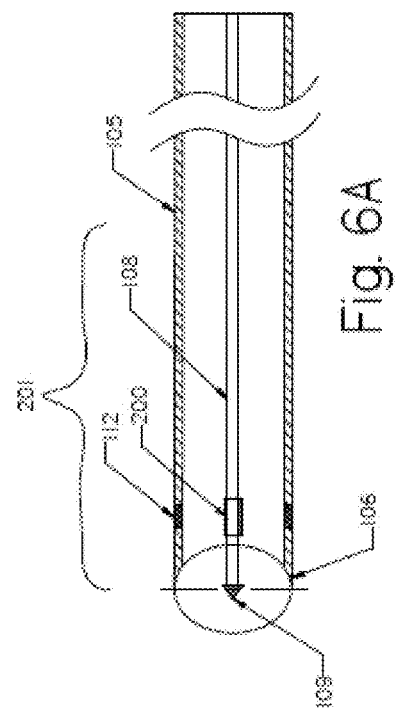
FIG. 6C shows the distal end of the rotational member positioned outside of the aspiration catheter.

FIG. 6C shows the distal end 106 of the aspiration catheter 105 and the distal portion 201 of the rotational member 108. The distance 601 between the distal tip 109 of the rotational member 108 and the distal end 106 of the aspiration catheter 105 when the distal tip 109 is inside the aspiration catheter 105 can range between 0.0 mm and 50 mm, most preferably between 0.0 mm and 5 mm as measured using any suitable visualization or intraoperative imaging. To simplify the positioning process, and to provide better visibility using any suitable visualization means, the distal portion 201 of the rotational member 108 and the distal end 106 of the aspiration catheter 105 can be made of radiopaque material. A radiopaque marker 112 can be positioned on the distal end 106 of the aspiration catheter 105 and another radiopaque marker 200 can be positioned on the distal end 201 of the rotational member 108. Often times, the aspiration catheter 105 will have to navigate a tortuous anatomy either within the endovascular system or outside the endovascular system, and the ability to position the distal tip 109 of the rotational member 108 correctly inside the distal end 106 of the aspiration catheter 105 may have a crucial impact on device safety and efficacy.

Figure 6D:
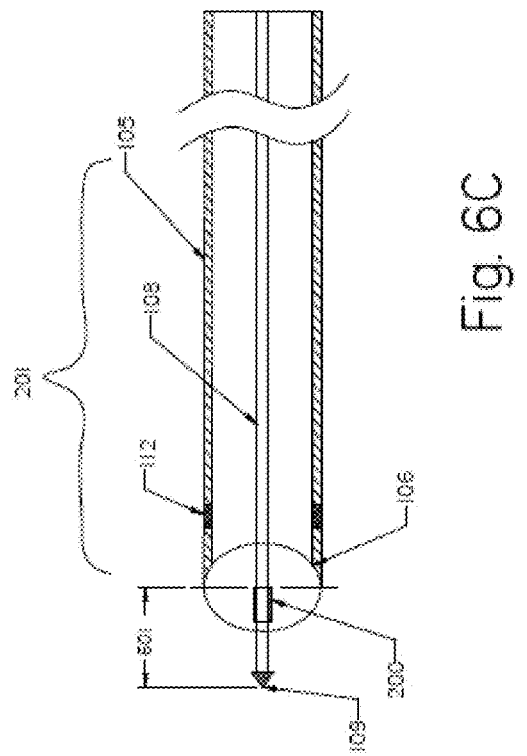
FIG. 6D shows a gap between the rotating distal end on the rotational member and the inside diameter of the aspiration catheter.

FIG. 6D shows the distal end 106 of the aspiration catheter 105 and the distal tip 109 of the rotational member 108. The distal tip 109 of the rotational member 108 is positioned inside the distal end 106 of the aspiration catheter 105. It is important that the radial gap 602 between the distal tip 109 of the rotating rotational member 108 and the wall of the inner lumen 206 at the distal end 106 of the aspiration catheter 105 is sufficient to not induce damages to the inner surface of the aspiration catheter 105. The gap 602 should be anywhere between 0.0 mm to 10 mm larger than the diameter of the internal lumen 206, with a preferred gap between 0.0 mm to 2 mm.

Adjustment of the distances 600 and 601 plays a very important role in the safe and efficient removal of thromboembolic material. During removal of well-organized clots (chronic clots) for example, the distal tip 109 of the rotational member 108 may be positioned outside the distal end 106 of the aspiration catheter 105 to macerate or disintegrate clots or other material before the material reaches the distal end 106 of the aspiration catheter 105, which is under vacuum during the thromboembolic material removal. Thus, this increases the system efficacy. In circumstances where procedural safety may be compromised, and exposure of the distal tip 109 of the rotational member 108 outside the distal end 106 of the aspiration catheter 105 might cause trauma or damage to the surrounding tissue, the distal tip 109 of the rotational member 108 may be repositioned accordingly using the fitting assembly 113 and the distance marks on the tube 202 as described hereinabove in FIGS. 1 and 2. The Touhy-Borst valve 204 may be positioned accordingly along the tube 202 to guarantee that the distal tip 109 of the rotational member 108 is inside the aspiration catheter 105. Such positioning of the Touhy-Borst valve 204 using distance marks on the tube 202 may be performed in addition to observing the alignment of the radiopaque marker 112 at the distal end 106 of the aspiration catheter 105 with the distal tip 109 using fluoroscopy or any other appropriate visualization method. The fitting assembly 113 provides adjustment for the distal tip 109 with respect to the distal end 106 of the aspiration catheter 105, so the distal tip 109 located inside the aspiration catheter 105 can be positioned therein so as to remain in contemporaneous position with the distal end 106 of the aspiration catheter 105 if necessary. The aspiration catheter 105 can be made of a polymer material and/or reinforced with a metal or polymer coiling, braiding and combinations of both, as well as including an internal lumen with a Teflon™ liner.

Figure 7C:
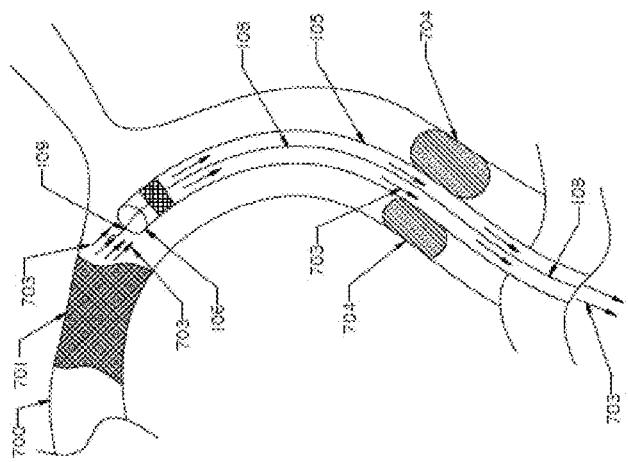
FIG. 7C is an enlarged view of the distal end of the aspiration catheter and the distal end of the rotational member of FIGS. 7A and 7B at the location of the clot undergoing aspiration.
Figure 7B:
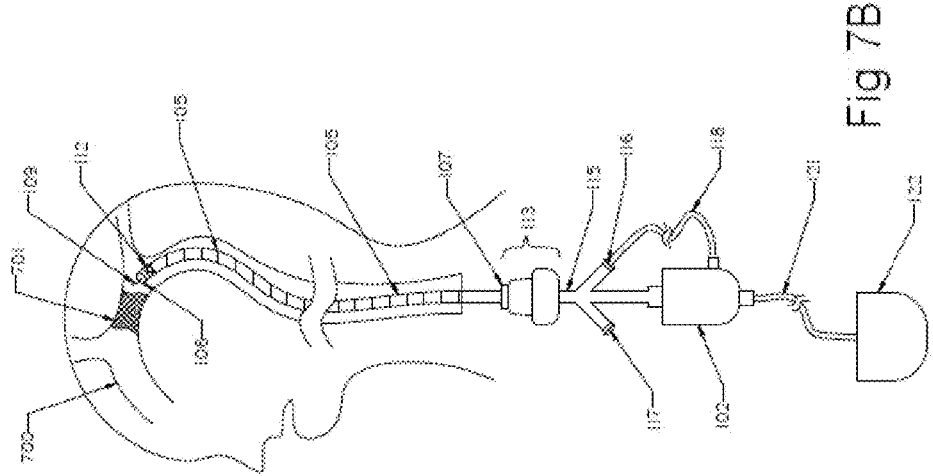
FIG. 7B is a cross sectional view illustrating the rotational member of the clot removal device positioned inside the aspiration catheter of FIG. 7A.
Figure 7A:
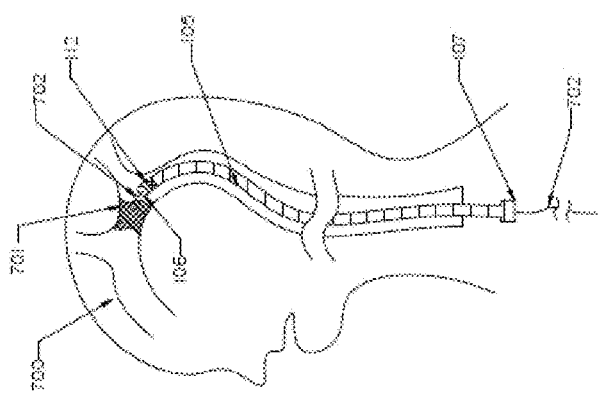
FIG. 7A is a cross-sectional view illustrating a placement of the aspiration catheter at the location of a clot within the human cerebral artery.

FIG. 7A shows an example of a patient suffering from Ischemic Stroke having blood clots located in the Middle Cerebral Artery (MCA) 700. The MCA is one of the three major paired arteries that supply blood to the cerebrum and arises from the internal carotid artery. Blood clots located in the M1 segment (sphenoidal segment) are the most common situations for patients treated with medical devices. Such blood clots located in the cerebrovascular circulation is identified in the hospital by symptoms, CT scan, MRI or fluoroscopic evaluation.

After the location of blood clots is confirmed, the aspiration catheter 105 is introduced to the cerebral vessel 700 and the treatment site 701 in such a way that the distal end 106 of the aspiration catheter 105 is in the vicinity of the blood clots to be removed. Introduction of the aspiration catheter 105 to the treatment site 701 can be done using a support element. Use of support elements is well known in the medical device field and includes, but is not limited to, use of guidewires, dilators, additional catheters, guiding catheters or combinations thereof. In FIG. 7A, the aspiration catheter 105 is introduced to the treatment site 701 operating in an over-the-wire approach using a conventional guidewire 702. The aspiration catheter 105 can also have a rapid exchange guidewire feature, and may be introduced to the treatment area in a rapid exchange fashion. After positioning the distal end 106 of the aspiration catheter 105 at the location of the blood clots, the guidewire 702 is removed. In the case where a rapid exchange guidewire is used, the guidewire may remain inside the body. The aspiration catheter 105 can be positioned in the body using one of the following approaches: through femoral approach, brachial approach, surgical approach from any feasible location including patient neck, radial approach, antegrade to the blood flow, or retrograde to the blood flow approach. The aspiration catheter 105 may be disconnected from the extraction device as shown in FIG. 2 or it may be any other suitable catheter that can access the treatment site 701.

Referring to FIG. 7B, after placing the aspiration catheter 105 in the cerebral artery 700 at the clot location 701 and removing the guidewire 702, the next step is to introduce the rotational member 108 of the extraction device 101 inside the aspiration catheter 105 such that the distal tip 109 of the rotational member 108 is adjacent the distal end 106 of the aspiration catheter 105, and within the catheter's distal-most end. After the rotational member 108 is positioned at the treatment location 701, activation of aspiration and rotation of the rotational member 108 will follow to initiate the removal of blood clots outside the patient. The rotational member 108 rotates along its longitudinal axis at a speed between 100 to 200,000 RPM, and is configured to break blood clots and facilitate the aspiration of blood clots outside the patient. To facilitate the efficient removal of blood clots, the distal end 106 of the aspiration catheter 105 can be repositioned relative to the distal tip 109 of the rotational member 108 at any time before or during the removal of blood clots. It is desirable that the distal tip 109 of the rotational member 108 remain in a contemporaneous position with the distal end 106 of the aspiration catheter 105. Also, the distal end of the extraction device 101 may be repositioned back and forth accordingly to ensure that blood clots are removed effectively. While the removal of the guidewire 702 from the aspiration catheter 105 after its placement at the blood clot location 701 is mentioned above, the guidewire 702 can also remain in place at the treatment location at a position that will not interfere with the rotational member 108. In such circumstances, a physician/operator would have quick access to the guidewire 702 when and if needed.

FIG. 7C shows a close-up view of the distal end 106 of the aspiration catheter 105 and the distal tip 109 of the rotational member 108 in the cerebral artery 700 at blood clot location 701 under aspiration, which is shown by the arrow 703. Thromboembolic material may be aspirated into the aspiration catheter 105 using a variety of aspiration modes, including but not limited to continuous aspiration, ON/OFF aspiration, modulated aspiration (Higher/Lower), or combinations thereof. FIG. 7C also shows an optional occlusion balloon 704 that provides at least a partial vessel seal around the area of thromboembolic material removal so as to minimize the aspiration of blood from neighboring vessels. The occlusion balloon 704 may be positioned proximal to the treatment area 701 as shown in FIG. 7C, or it can be positioned distal to the treatment area (not shown), or occlusion balloons can be position distal and proximal to the treatment location 701 (not shown). To ensure a better positioning of the extraction device 101 at the treatment location 701, the aspiration catheter 105 may have a smaller distal dimension than its proximal dimension. The removal of thromboembolic material may also include infusing the vessel or treatment site with fluid (e.g., sodium chloride, thrombolytic agent or therapeutic drug) to assist in the disintegration of, or to break up, the clot or tissue into a particle size that can then be more easily and quickly aspirated through a lumen of the aspiration catheter 105. Thrombolytic agents may include, but are not limited to: tissue plasminogen activator, blood clot reducing agents, antiplatelet agents, and other GIIb/IIIa inhibitors.

When the extraction device 101 is positioned at a treatment area with a complex access (such as cerebrovascular circulation) or in area with a simple access (such as AV fistula), the rotational member 108 traverses concomitant bends as the aspiration catheter 105 during their introduction to the treatment area and during the removal of thromboembolic material.

FIG. 8A is a close-up view of the aperture 117 located on the 3 way Y-connector 115, which is shown as having a circular opening 800. FIG. 8B shows the opening 800 closed using the operator's finger 801. Vacuum pressure pulsation can be achieved using any aperture within the extraction device 101 which normally is a well-sealed passageway structure between the distal end 106 of the aspiration catheter 105 (inlet) and the outlet 120 of the vacuum pump 103 as shown in FIG. 1. The operator can manually open and close the opening 800 using a finger. Opening and covering the opening 800 (ON/OFF) will produce pulsing vacuum pressure at the distal end 106 of the aspiration catheter 105. The aperture 117 may have a regular opening configuration, including but not limited to, circular 800 (as shown), oval, square, rectangular, octagonal, hexagonal, or any non-regular configuration that can be conveniently covered by a finger. The ON or open time duration of the aperture 117 may be anywhere between 0.01 to 10 seconds. The OFF or closed time of the aperture 117 may also be in the same range of 0.01 to 10 seconds. Any combination of ON and OFF time is suitable for clot removal according to the present invention.

FIG. 9A is a close-up view of the aperture 117 having a longitudinal incision opening 900. Vacuum pressure modulation at the distal end 106 of the aspiration catheter 105 can be achieved in a similar way as the pulsation described above in connection with FIGS. 8A-8B. Different openings may be used for the aperture 117, including but not limited to: longitudinal incision 900 (as shown), slit or notch. Such incision opening 900 will allow the operator to move the finger 901 along the opening 900 so as to increase or decrease the size of the opening 900 as shown in FIG. 9B. Increasing and decreasing finger coverage over the incision 900 will produce pressure modulation at the distal end 106 of the aspiration catheter 105, and change compliance of the clots. The speed of the movement of the finger 901 along the opening 900 depends on the desired aspiration modulation characteristics and may result in full opening and closure of the opening 900, partial opening and closure of opening 900, and can also be combined with ON/OFF pulsing.

FIG. 10 is a close-up view of the distal end 106 of the aspiration catheter 105 positioned at the clot location 1000. Arrows 1001 illustrate pulsation or modulation stress applied by the vacuum displayed by arrow 1002 from within the catheter 105. Closing and opening the aperture 117 by the operator will cause ON/OFF stress on the clots 1000, weakening their structure by inducing fractures causing internal/external clot separation 1003. This illustrates the changing of the compliance of the clots 1000, thereby accelerating removal of the clots through the aspiration catheter 105 outside the patient.

Providing a saline flush during blood clot removal may greatly improve clot clearing by flushing clots to the blood container. Delivery of liquid during clot removal may be by achieved by flushing the extraction device 101, providing continuous flush distally to the clot removal area, or a combination of both.

Use of negative suction pressures to achieve liquid transfer, air transfer or aspiration can be accomplished by a number of different methods depending on the mechanical pump design used. These pump designs can include piston pumps, diaphragm pumps, gear pumps or peristaltic pumps. In some liquid or air handling systems, pumps may utilize a pressurized reservoir to create the vacuum for further suction and collection of liquids. Other forms of liquid or air handling system utilize flow-through pumps and are considered stand-alone devices. From a clinical perspective, pumps for removal of clots, liquids or tissue from the human body using flow-through are considered single-use devices. Such pumps become contaminated after use and should be disposed of. Other pumps that utilize pressurized reservoirs can be reused and only suction collection containers need to be disposed of after a clinical procedure. The spirit of the present invention is not limited to use of a disposable suction pump or a reusable aspiration pump that utilizes suction containers, but can also include any other source of suction, such as a hospital's central aspiration system.

While there are some physical limitations related to the operator's ability of opening or closing the aspiration aperture, or moving a finger along the incision at higher speed, simple electromechanical or electromagnetic devices can also be helpful to achieve a higher frequency pulsation and modulation.

Figure 11:
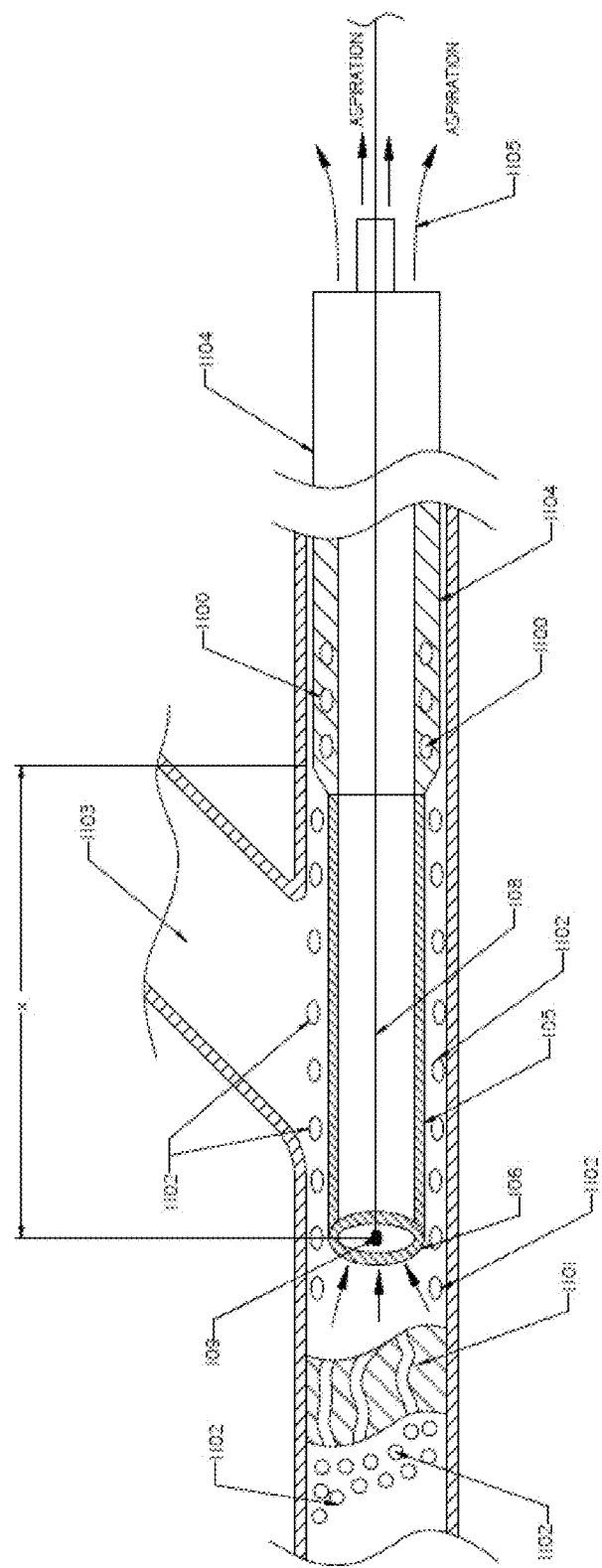
FIG. 11 illustrates the extraction device with a dual aspiration to prevent emboli from migrating distally or into side branches.

Alternatively, an additional aspiration source 1100 may be positioned over or around the aspiration catheter 105 at a location within the distance x from the distal end 106, shown in FIG. 11. This distance x can be 1-10 cm from the distal end 106 to further prevent dislodgement of small emboli 1102 from clot 1101, or distal movement or flooding into other vascular branches 1103 as shown in FIG. 11. Such additional aspiration source 1100 can be a conventional guiding catheter 1104 or another catheter or sheath routinely used for such procedure. An external aspiration source (not shown) can be attached to the proximal outlet 1105 of the aspiration catheter 105, and the proximal outlet of the guiding catheter 1104. This dual-aspiration approach will assure that any emboli created during removal of blood clots will be further aspirated through the secondary aspiration source 1100.

Some embodiments of the present invention include cooling of brain tissue before, during or after the removal of thromboembolic material. For example, cooling brain tissue may involve local endovascular cooling, cooling the patient's neck, cooling the patient's head and/or cooling the patient's body.

Elements or components shown with any embodiment herein are exemplary for the specific embodiment and may be used on or in combination with other embodiments disclosed herein. The invention is susceptible to various modifications and alternative forms and should not be limited to the particular forms or methods disclosed. To the contrary, the invention is to cover all modifications, equivalents and alternatives thereof.

Some scientific and theoretical descriptions have been provided as the mechanism by which the devices and therapeutic methods are effective; these descriptions have been provided only for the purpose of conveying an understanding of the invention, and have no relevance to or bearing on claims made to this invention.

Some theoretical considerations have been provided as to the mechanism by which these therapeutic methods are effective; these considerations have been provided only for the purpose of conveying an understanding of the invention, and have no relevance to or bearing on claims made to this invention.

The scope of the claims appended hereto is not limited by any of the particular embodiments described below. For example, in any method or process disclosed herein, the acts or operations of the method or process may be performed in any suitable sequence and are not necessarily limited to any particular disclosed sequence.

What is claimed is:

1. An extraction device for removing thromboembolic material from a patient, comprising:
   a drive unit; an elongated rotational member rotates within 100 to 500,000 rpm:
   the elongated rotational member has a proximal end that is connected to the drive unit, and a distal tip having a shaped configuration, wherein the rotational member comprises at least one longitudinal element selected from the group consisting of: a single solid rod, multiple solid rods, coil, a braid, strands and cable: and
   an aspiration catheter at least partially surrounding the rotational member and having an aspiration passage;
   wherein the rotational member traverses concomitant bends as the aspiration catheter during a therapeutic procedure, and rotates with respect to the aspiration catheter when the drive unit is actuated; wherein further including a fitting assembly; and wherein the fitting assembly includes a Y-connector, a rigid tube and a stopper positioned on the rigid tube to prevent the distal tip of the rotational member from being exposed outside the aspiration catheter.

2. The device of claim 1, wherein the shaped configuration positioned at the distal tip of the rotational member has a radial diameter that is larger than the dimension of an adjacent proximal portion of the rotational member.

3. The device of claim 1, wherein the drive unit includes at least one of the following: an aspiration pump, an electrical motor, or both.

4. The device of claim 1, wherein the rotational member circles distally using one of the following motions: angular motion, reciprocal motion, off-centered motion, or combinations thereof.

5. The device of claim 1, wherein the structure of the rotational member comprises polymer, metal, metal alloys or combinations thereof.

6. The device of claim 1, wherein shaped configuration of the distal tip of the rotational member is selected from the group consisting of: winged, quarter sinusoidal, half-sinusoidal, finned, blade, hook, loop, basket, bend, coil and braid.

7. The device of claim 1, wherein the aspiration catheter is one of the following: an integral part of the extraction device, or detachable from the extraction device.

8. The device of claim 1 wherein the aspiration catheter is fluidly coupled with an aspiration pump.

9. The device of claim 1, wherein the aspiration catheter has a separate guidewire lumen.

10. The device of claim 1, wherein the aspiration catheter and the rotational member are further configured to deliver radiofrequency for the blood vessel or for tissue cauterization.

11. The device of claim 1, wherein the gap formed between the radial diameter of the rotational member and inner diameter of the aspiration catheter is between 0 and 5 mm.

12. The device of claim 1, further comprising a radiopaque marker positioned at one of the following locations: on the distal end of the aspiration catheter, on the distal end of the rotational member, or at both locations.

13. The device of claim 1, wherein the distal tip of the rotational member is housed in a one of the following locations: inside the aspiration catheter, outside of the aspiration catheter, even with the aspiration catheter, or moveable between the inside and outside of the distal end of the aspiration catheter.

14. The device of claim 1, further comprising an aperture along the extraction device in fluid communication with the aspiration catheter and configured to regulate the level of the vacuum used for aspiration.

15. The device of claim 1, wherein the rotational member has a profile selected from the group consisting of: continuous diameter along its length, tapered along its entire length, tapered along the distal portion in a distal direction, at least partially tapered in the proximal direction, multi-tapered, and combinations thereof.

16. The device of claim 1, wherein the rotational member transmits torque in one of the following directions: one direction clockwise, one direction counterclockwise, or both directions.

17. The device of claim 16, wherein rotational member rotates in one of the following modes: continuous, modulated, ON/OFF.

18. The device of claim 16, wherein the distal tip of the rotational member applies centripetal forces to the thromboembolic material.

19. The device of claim 16, further including a separate guidewire lumen.

* * * * *